(12) United States Patent
Gu et al.

(10) Patent No.: US 11,617,868 B2
(45) Date of Patent: Apr. 4, 2023

(54) OBLIQUE INFLATION TYPE BALLOON CATHETER AND BALLOON BASE

(71) Applicants: NATIONAL UNIVERSITY CORPORATION KOBE UNIVERSITY, Kobe (JP); FUJI SYSTEMS CORPORATION, Tokyo (JP)

(72) Inventors: Eisei Gu, Kobe (JP); Takumi Fukumoto, Kobe (JP); Fumikazu Watanabe, Yokohama (JP); Akihiro Asai, Yokohama (JP)

(73) Assignees: NATIONAL UNIVERSITY CORPORATION KOBE UNIVERSITY, Kobe (JP); FUJI SYSTEMS CORPORATION, Tokyo (JP)

( * ) Notice: Subject to any disclaimer, the term of this patent is extended or adjusted under 35 U.S.C. 154(b) by 1075 days.

(21) Appl. No.: 16/088,635

(22) PCT Filed: Mar. 30, 2016

(86) PCT No.: PCT/JP2016/060359
§ 371 (c)(1),
(2) Date: Sep. 26, 2018

(87) PCT Pub. No.: WO2017/168627
PCT Pub. Date: Oct. 5, 2017

(65) Prior Publication Data
US 2019/0366058 A1 Dec. 5, 2019

(51) Int. Cl.
*A61M 25/10* (2013.01)
*A61M 25/00* (2006.01)

(52) U.S. Cl.
CPC .... *A61M 25/1002* (2013.01); *A61M 25/0017* (2013.01); *A61M 25/104* (2013.01); *A61M 25/1018* (2013.01); *A61M 2205/3331* (2013.01)

(58) Field of Classification Search
CPC .......... A61M 25/1002; A61M 25/0017; A61M 25/1018; A61M 25/104; A61M 2205/3331
(Continued)

(56) References Cited

U.S. PATENT DOCUMENTS

| 4,886,059 A | 12/1989 | Weber |
| 5,076,268 A | 12/1991 | Weber |

(Continued)

FOREIGN PATENT DOCUMENTS

| CN | 201135683 Y | 10/2008 |
| CN | 201814973 U | 5/2011 |

(Continued)

OTHER PUBLICATIONS

Notification of Grant issued in corresponding Chinese Patent Application No. 201680083231.0 dated Sep. 4, 2020 (in Chinese only).
(Continued)

*Primary Examiner* — Andrew J Mensh
(74) *Attorney, Agent, or Firm* — Troutman Pepper Hamilton Sanders LLP

(57) ABSTRACT

The balloon catheter of the present invention is provided with a balloon base at a front end of a tubular catheter body having a predetermined length. The balloon base includes a cylindrical base having a larger diameter than an outer diameter of the catheter body, and a lumen having substantially the same diameter as the outer diameter of the catheter body is formed on the base over an entire length with both ends opened. A central axis of the lumen is inclined at a predetermined angle with respect to a central axis of the base (Continued)

concentric with a central axis of the catheter body, and an outer peripheral surface is formed in parallel with the central axis of the base. The balloon is provided on the outer peripheral surface of the parallel base to obliquely inflate with respect to the central axis of the catheter body during inflation.

4 Claims, 5 Drawing Sheets

(58) Field of Classification Search
USPC .......................................................... 604/6.16
See application file for complete search history.

(56) References Cited

U.S. PATENT DOCUMENTS

| | | | |
|---|---|---|---|
| 5,250,029 | A | 10/1993 | Lin et al. |
| 6,152,136 | A | 11/2000 | Pagan |
| 6,526,977 | B1 | 3/2003 | Goebel |
| 8,460,240 | B2 | 6/2013 | Towler |
| 2008/0086083 | A1 | 4/2008 | Towler |
| 2009/0090366 | A1 | 4/2009 | Cuevas et al. |
| 2009/0254064 | A1 | 10/2009 | Boatman |
| 2013/0331814 | A1* | 12/2013 | Fulton, III .......... A61M 1/3615 604/500 |

FOREIGN PATENT DOCUMENTS

| | | |
|---|---|---|
| JP | H10-328303 A | 12/1998 |
| JP | 2002-505926 A | 2/2002 |
| JP | 2003250900 A | 9/2003 |
| JP | 2006305025 A | 11/2006 |
| JP | 2010500111 A | 1/2010 |
| JP | 2012-200573 A | 10/2012 |
| JP | 5679813 B2 | 1/2015 |
| WO | 00/67656 A1 | 11/2000 |

OTHER PUBLICATIONS

International Search Report dated Jun. 21, 2016 during the prosecution of PCT/JP2016/060359.
Notification of Grant issued in corresponding Japanese Patent Application No. 2017-172769 dated Dec. 19, 2017. (with English translation).

* cited by examiner

OBLIQUE INFLATION TYPE BALLOON CATHETER AND BALLOON BASE

CROSS-REFERENCE TO RELATED APPLICATION

This is a U.S. national phase application under 35 U.S.C. § 371 of International Patent Application No. PCT/JP2016/060359, filed Mar. 30, 2016. The entire contents of these applications are hereby incorporated by reference.

FIELD OF TECHNOLOGY

The present invention relates to an oblique inflation type balloon catheter and a balloon base, and more specifically relates to a balloon catheter, which is indwelled mainly in a blood vessel, capable of preventing a blood flow from directly hitting against a blood vessel wall by allowing a balloon provided at a distal end of a catheter body to obliquely inflate even in a curved blood vessel and capable of suppressing occurrence of a wrinkle in a balloon deflated state, and a balloon base for attaching the balloon.

BACKGROUND

In general, the balloon provided on the balloon catheter is adapted to inflate concentrically with respect to the catheter body. Therefore, in the case of a linear blood vessel, since the balloon is positioned at a right angle to the blood vessel, indwelling fixation is excellent, and a catheter lumen faces a center of the blood vessel against the blood vessel, so that it is possible to smoothly send blood or deliver liquid.

For example, the balloon catheter described above is used for a mass administration system of an anticancer drug to a liver cancer patient known as percutaneous hepatic perfusion chemotherapy (PIHP: Percutaneous Isolated Hepatic Perfusion). This system selectively removes an anticancer drug largely administered in a hepatic artery from a hepatic vein together with blood, adsorbs and removes the anticancer drug using an activated carbon column, etc., and then sends the blood to a patient again. For this reason, in the system, as illustrated in FIG. 12, while the anticancer drug is continuously administered into the hepatic artery using a catheter 105 of an anticancer drug administration device, two balloons 103 and 104 of a balloon catheter 101 separately inserted into the blood vessel of the patient occlude upper and lower portions near a branch of the hepatic vein, and the anticancer drug largely administered from the hepatic artery is taken in together with hepatic venous blood as indicated by an arrow from a side hole provided in a part occluded by the both balloons. Thereafter, blood is removed from a blood removal lumen (not illustrated), purified through a pump P and a blood purifier F outside a body, and returned to a blood feeding lumen (not illustrated). Then, the purified and returned blood bypasses a part occluded by the balloons 103 and 104 and is sent from a distal end opening of the balloon catheter 101 to a heart.

Incidentally, in the PIHP therapy, it is necessary to indwell a distal end balloon in a short curved blood vessel portion between the heart and three hepatic vein holes (a right hepatic vein opening, a middle hepatic vein opening, and a left hepatic vein opening) to completely block a blood flow in the inferior vena cava following a right atrium of the heart using the balloon catheter 101. When the balloon catheter is inserted into and indwelled in the curved blood vessel, as illustrated in FIG. 13, a central axis of the lumen of the curved blood vessel is shifted from a central axis of the balloon catheter 101 due to an influence of the rigidity of the balloon catheter, and there is a danger that the blood flow directly hits the blood vessel wall as illustrated in the figure and damages the blood vessel wall. In addition, depending on the shape of the blood vessel wall, there is a problem that a contact area of the balloon decreases and the balloon tends to slip due to pressure during blood feeding. Further, there is problem that the balloon may not adhere to the blood vessel wall to generate a gap due to an anatomical individual difference such as a shape of a blood vessel/a degree of curvature/a position of a hepatic vein hole, etc., and a large amount of administered anticancer drug enters circulation blood and is carried to the whole body. In this way, when the balloon catheter is inserted into and indwelled in the curved blood vessel and the blood flow is blocked by the balloon, there are problems of blood vessel wall damage due to a blood flow, balloon slipping due to a decrease in balloon contact area, and incomplete occlusion of the blood vessel (incomplete blockage of a blood flow).

According to investigation by the applicant, a prior art document for solving such problems is not present. However, JP 5679813 B2 discloses a balloon used for a tracheostomy tube inserted into a tracheal lumen.

Registered Japanese Patent No. JP 5679813 B2 relates to a tracheostomy tube device and is an invention having a balloon below according to description in claim 1, FIG. 4, etc. That is, a balloon 175 disclosed herein is an inflatable balloon surrounding a part of a hollow tube 155. The balloon 175 includes a balloon distal end 180 attached to a distal end 165 of the tube by positioning the distal end of the tube substantially at a center of the balloon and a balloon proximal end 185 located below away from a head of a patient farther than a proximal face P of the device and attached to a bending region 170 of the tube by separating a center of the bending region from substantially the center of the balloon by 8 mm to 10 mm to a front side of the patient. At the time of inflation, the balloon 175 inflates around the distal end of the tube and a proximal end 160 of the tube located below the proximal face of the device to occlude a trachea below a trachea fistula without occluding the trachea fistula (reference numerals are attached for reference).

However, since the balloon 175 is a balloon formed by preliminary shaping in a configuration described above with respect to a catheter body, a wrinkle is formed in a deflated state, and unevenness due to the balloon is generated on a surface of the catheter body, so that adhesion to the surface is not allowed. For this reason, when the catheter having the balloon with unevenness formed on the surface due to the wrinkle is inserted into the blood vessel as the above-mentioned mass administration system, there is concern that an inner wall of the blood vessel may be damaged by unevenness due to the wrinkle of the balloon. Besides, similarly to the conventionally known balloon described above, the problem that the balloon easily slips may not be solved.

SUMMARY

In this regard, an object of the present invention to provide an oblique inflation type balloon catheter in which a balloon may be obliquely inflated to tilt with respect to a catheter body without a central axis of a blood vessel being shifted from a central axis of a catheter body even when the blood vessel is curved, and rarely slips without a contact area with respect to the blood vessel decreasing and a wrinkle being formed on the balloon in a deflated state, and a balloon base by solving the conventional problems described above.

To solve the above-mentioned problems, the invention can be a balloon catheter in which a balloon is provided at a front end of a tubular catheter body having a predetermined length, wherein a balloon base having a larger diameter than an outer diameter of the catheter body is integrally provided in a cylindrical shape at the front end of the catheter body, the balloon base is formed such that an outer peripheral surface thereof in an axis direction is inclined at a predetermined angle with respect to a central axis of the catheter body, and the balloon is provided on the outer peripheral surface to obliquely inflate with respect to the central axis of the catheter body during inflation.

The invention can also be a balloon catheter in which a balloon is provided at a front end of a tubular catheter body having a predetermined length, wherein a balloon base is provided at the front end of the catheter body, the balloon base includes a balloon and a base and includes a cylindrical base having a larger diameter than an outer diameter of the catheter body, a lumen having substantially the same diameter as the outer diameter of the catheter body is formed on the base over an entire length with both ends opened, a central axis of the lumen is inclined at a predetermined angle with respect to a central axis of the base concentric with a central axis of the catheter body, an outer peripheral surface in an axis direction is formed in parallel with the central axis of the base, and the balloon is provided on the outer peripheral surface of the parallel base to obliquely inflate with respect to the central axis of the catheter body during inflation.

Alternately, the lumen of the catheter body is partitioned into a blood removing lumen for removing blood from a blood vessel and a blood feeding lumen for sending blood to the blood vessel, and an opening area of the blood removing lumen is larger than an opening area of the blood feeding lumen.

Also, a second balloon is provided in the catheter body at a predetermined length behind the balloon, and a side hole for taking blood into the blood removing lumen is provided in the catheter body between the second balloon and the balloon as described above.

Further, the predetermined angle is in a range of 3° to 10°.

The invention can be described as a balloon base provided at the front end of the catheter body in the oblique inflation type balloon catheter according to any one of the above examples, wherein the base includes a cylindrical base having a larger diameter than an outer diameter of the catheter body, a lumen having substantially the same diameter as the outer diameter of the catheter body is formed on the base over an entire length with both ends opened, a central axis of the lumen is inclined at a predetermined angle with respect to a central axis of the base, and an outer peripheral surface in an axis direction is formed in parallel with the central axis of the base.

As above, the predetermined angle is in a range of 3° to 10°.

Additionally, the outer peripheral surface includes an outer peripheral surface of a balloon attachment central portion parallel to the central axis of the base and an outer peripheral surface of both ends curved to have a diameter gradually decreasing from the portion described above.

A communication passage allows communication between the inside of the balloon and a balloon lumen provided on a peripheral wall of the catheter body is formed in the balloon base in any one of the above examples.

The invention is as described above and a balloon base having a larger diameter than an outer diameter of the catheter body is integrally provided in a cylindrical shape at the front end of the catheter body, the balloon base is formed such that an outer peripheral surface thereof in an axis direction is inclined at a predetermined angle with respect to a central axis of the catheter body, and the balloon is provided on the outer peripheral surface to obliquely inflate with respect to the central axis of the catheter body during inflation.

In addition, a balloon base is provided at the front end of the catheter body, the balloon base includes a substantially tubular shaped-base having a larger diameter than an outer diameter of the catheter body, a lumen having substantially the same diameter as the outer diameter of the catheter body is formed on the base over an entire length with both ends opened, a central axis of the lumen is inclined at a predetermined angle with respect to a central axis of the base concentric with a central axis of the catheter body, an outer peripheral surface is formed in parallel with the central axis of the base, and the balloon is provided on the outer peripheral surface of the parallel base to obliquely inflate with respect to the central axis of the catheter body during inflation. Thus, in either case, the balloon may obliquely inflate with respect to the catheter body. For this reason, even in a curved blood vessel, a central axis thereof does not shift from the central axis of the catheter body. Therefore, unlike the conventional one, the central axis of the lumen of the curved blood vessel does not shift from the central axis of the catheter, and the blood flow does not directly hit the blood vessel wall to damage the blood vessel wall due to the rigidity of the catheter. In addition, at the same time, a contact area of the balloon with respect to the blood vessel does not decrease, and adhesion to the outer peripheral surface of the base is allowed since the balloon is not shaped and a wrinkle is not formed even in a balloon deflated state. Therefore, the balloon does not slip due to pressure during blood feeding, and there is an effect that indwelling and fixing may be firmly performed. Further, there are effects that an oblique inflation direction of the balloon may be adjusted by rotating a catheter central axis according to an anatomical individual difference such as a curved shape or a position of a hepatic vein ostium in a short blood vessel lumen between the heart and the liver during use, and the balloon on the distal end side may be appropriately indwelled and fixed. On the other hand, in a conventional balloon incapable of inflating in an oblique direction, a contact position between a balloon and a blood vessel lumen may not be changed even when a central axis of a catheter is rotated.

According to the invention, since the lumen of the catheter body is partitioned into a blood removing lumen for removing blood from a blood vessel and a blood feeding lumen for sending blood to the blood vessel, and an opening area of the blood removing lumen is larger than an opening area of the blood feeding lumen, it is possible to rapidly, surely, and efficiently remove blood.

According to the invention, since a second balloon is provided in the catheter body at a predetermined length behind the balloon, and a side hole for taking blood into the blood removing lumen is provided in the catheter body between the second balloon and the balloon, it is possible to effectively withdraw blood between the both balloons from the side hole to the blood removing lumen.

According to the invention, since the predetermined angle is in a range of 3° to 10°, it is possible to effectively deal with a curved blood vessel of a patient having some individual differences.

According to the invention, since the base includes a cylindrical base having a larger diameter than an outer diameter of the catheter body, a lumen having substantially the same diameter as the outer diameter of the catheter body is formed on the base over an entire length with both ends opened, a central axis of the lumen is inclined at a predetermined angle with respect to a central axis of the base, and an outer peripheral surface in an axis direction is formed in parallel with the central axis of the base, the balloon attached to the outer peripheral surface with the base interposed therebetween may be inflated to be inclined with respect to the catheter body.

According to the invention, since the predetermined angle is in a range of 3° to 10°, it is possible to effectively deal with a curved blood vessel of a patient having some individual differences.

According to the invention, since the outer peripheral surface includes an outer peripheral surface of a balloon attachment central portion parallel to the central axis of the base and an outer peripheral surface of both ends curved to have a diameter gradually decreasing from the portion, it is possible to smoothly attach the balloon to the outer peripheral surface of the central portion, and to prevent damage to the blood vessel wall by the outer peripheral surface of the curved both ends.

According to the invention, since a communication passage for communication between the inside of the balloon and a balloon lumen provided on a peripheral wall of the catheter body is formed in the balloon base, the balloon may be inflated and deflated through the communication passage even when the balloon is attached with the base interposed therebetween.

BRIEF DESCRIPTION OF DRAWINGS

FIGS. 4A, 4B, 4C and 4D illustrate a balloon base, FIG. 4 is a rear view, FIG. 4 is a left side view, and FIG. 4 is a right side view.

DETAILED DESCRIPTION

Hereinafter, an oblique inflation type balloon catheter according to an embodiment of the present invention will be described with reference to drawings.

Figure 1:
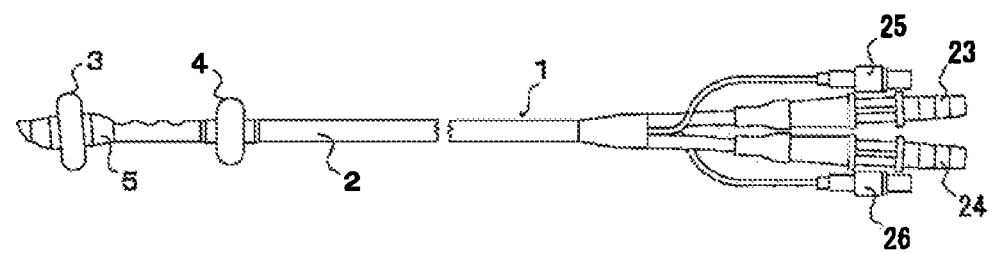
FIG. 1 is a front view of an oblique inflation type balloon catheter according to an embodiment of the present invention in which a part of a length of a catheter body is omitted.
Figure 2:
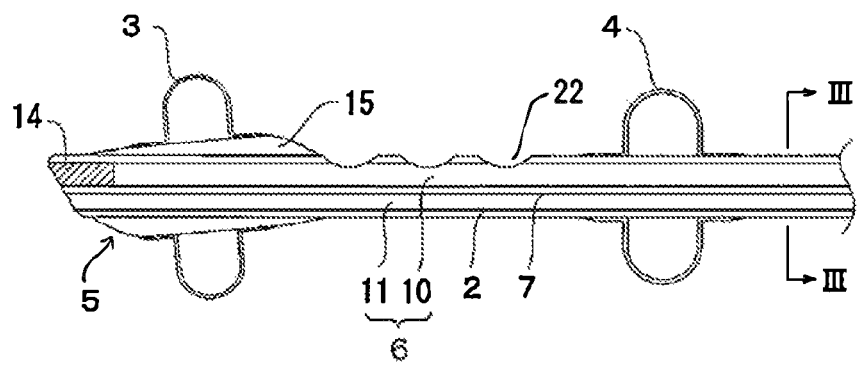
FIG. 2 is an enlarged cross-sectional view of a balloon portion of the same.
Figure 3:
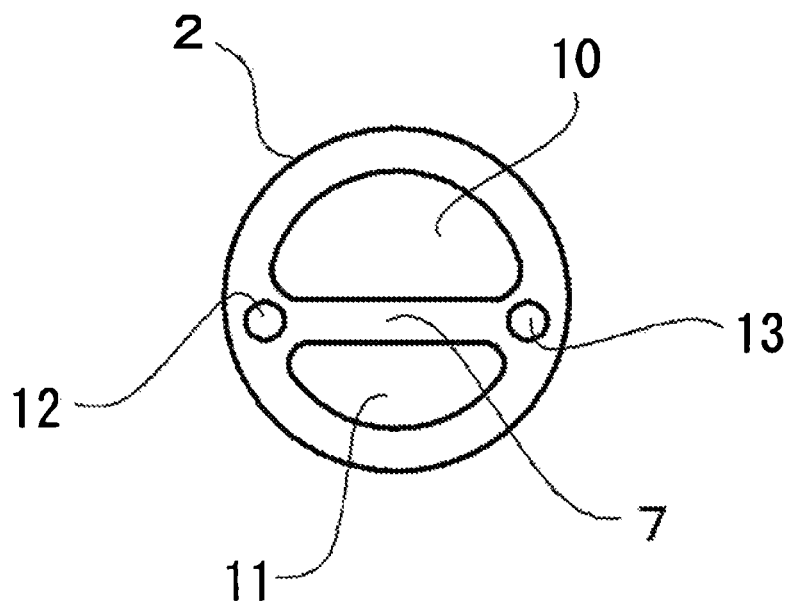
FIG. 3 is an enlarged cross-sectional view taken along III-III line of FIG. 2.

In FIGS. 1 to 3, reference numeral 1 denotes a balloon catheter made of a material suitable for a living body such as silicone rubber. The balloon catheter 1 mainly includes a tubular catheter body 2, balloons 3 and 4, and a balloon base 5.

In the catheter body 2, a lumen 6 having a substantially circular cross section is provided in an axis direction from a front end to a rear end thereof. A front end of the catheter body 2 is obliquely cut out. The lumen 6 is partitioned into a blood removing lumen 10 and a blood feeding lumen 11 by an integrally formed partition wall 7 extending in an axial direction. The blood removing lumen 10 is for removing blood from a blood vessel in a body, and the blood feeding lumen 11 is for sending blood to the blood vessel in reverse. In this example, an opening area of the blood removing lumen 10 on a surface orthogonal to the axial direction is slightly larger than that of the blood feeding lumen 11. A reason therefor is to carry out blood removal more rapidly, surely and efficiently. A ratio of the opening area of the blood removing lumen 10 to the opening area of the blood feeding lumen 11 is not particularly limited, and is preferably 6:4 ratio in terms of ratio. In this example, the blood removing lumen 10 and the blood feeding lumen 11 are partitioned by the partition wall 7. However, a small-diameter pipe may be concentrically arranged in the lumen 6 without partitioning by the partition wall 7, and an inside or an outside of the pipe may be used as either the blood removing lumen 10 or the blood feeding lumen 11.

As illustrated in FIG. 3, a lumen 12 for the balloon 3 at the front and a lumen 13 for the balloon 4 at the rear are formed along the axis direction on a wall of the catheter body 2 near both proximal ends of the partition wall 7, and communicate with the balloons 3 and 4 through a communication passage (described below) provided in the balloon base 5, respectively. Physiological saline, etc. is injected from a syringe, etc. (not illustrated) into each of the lumens 12 and 13 to allow inflation and deflation of the balloons 3 and 4 communicating therewith through the communication passage. In FIG. 2, reference numeral 14 denotes a rod-like filling as a padding material which is filled in a front end opening of the blood removing lumen 10 to close the opening.

The balloon base 5 includes a component independently manufactured separately from the catheter body 2 and is provided at a front end of the catheter body 2. This balloon base 5 has of an eccentric type single lumen tube type. That is, as specifically illustrated in FIGS. 4(A) to 4(D) and FIG. 5, the balloon base 5 includes a base 15 which has a diameter larger than an outer diameter of the catheter body 2, is formed in a substantially tubular shape, and has a predetermined length, and a lumen 16 having substantially the same diameter as the outer diameter of the catheter body 2 is formed on the base to open at front and rear ends thereof.

When the base is provided at the front end of the catheter body 2, the lumen 16 on the base 15 is provided such that a central axis X thereof is inclined at a predetermined angle θ° with respect to a central axis Y of the base 15 which is concentric with the central axis of the catheter body 2. This angle of inclination is preferably in a range of 3° to 10°, particularly preferably 4° to 6°, and more particularly preferably 5° in this example. The angle of inclination is not limited to the angle in the range of 3° to 10°, and may be set to an arbitrary angle around the range, particularly in a range of an angle of 16° to 25° for a large angle as necessary since there is an individual difference in degree of curvature of a blood vessel depending on the patient. When the lumen 16 is inclined as described above, a front end opening thereof is located closer to an upper side of the base 15, and a rear end opening is located closer to a lower side of the base 15.

At a central portion of the base 15, two water passing holes 17 are provided as communication passages for communication between the inside of the balloon 3 and the balloon lumen 12 provided on a peripheral wall of the catheter body 2.

The base 15 includes a central portion 18 which is an outer peripheral surface parallel to the central axis Y of the base 15 concentric with the central axis of the catheter body 2 as described above and both ends 19 and 20 which are outer peripheral surfaces curved in tapered shapes to have diameters gradually decreasing from the portion. Further, the balloon 3 is provided on the outer peripheral surface of the central portion 18 which is parallel. The both ends 19 and 20 have a large degree of curvature on a thicker side and a small degree of curvature on a thinner side. As is clear from FIG. 5, the balloon base 5 is formed in a point-symmetrical shape centered on a center point P, and a right half and a left half have bilateral symmetry at 180° opposite positions.

Figure 4:
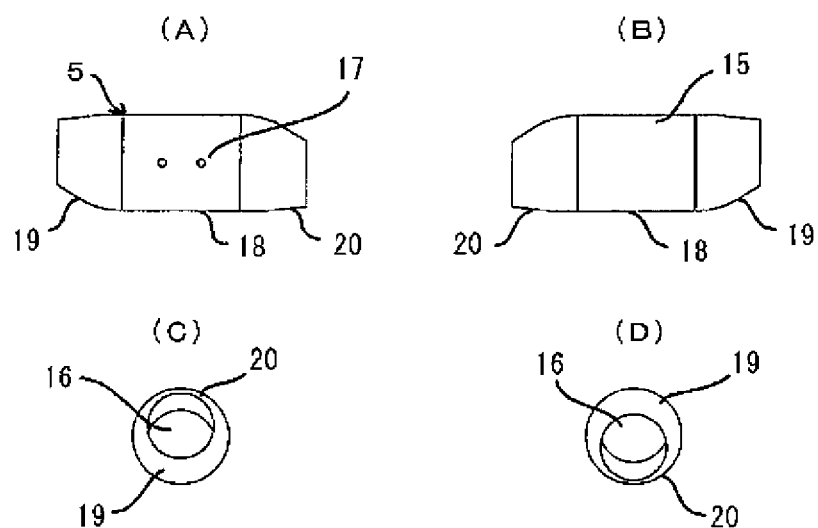
FIG. 4 is a front view.
Figure 5:
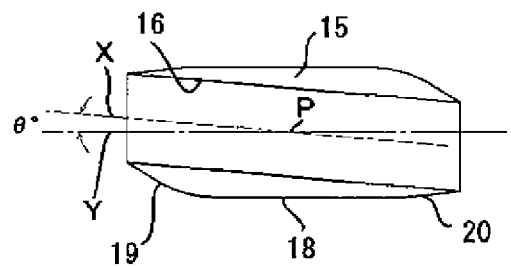
FIG. 5 is an enlarged cross-sectional view of the balloon base.

Due to the above-described shape, the balloon base 5 is viewed from the left side in a shape in which the front end opening of the lumen 16 faces upward to face the inside of the lumen as illustrated in FIG. 4(C), and is viewed from the right side in a shape in which the rear end opening of the lumen 16 faces downward to face the inside of the lumen as illustrated in FIG. 4D.

When dimensions of each component of the balloon base 5 are described for reference, the total length is 30 mm, the outer diameter is 11.7 mm, the diameter of the lumen 16 is 8 mm, the length of the central portion 18 is 17 mm, the length of both ends 19 is 8.6 mm, and the length of both ends 20 is 5.0 mm.

As described above, in the catheter body 2 between the balloon 4 and the balloon 3 in which the balloon base 5 provided with the balloon 3 is provided at the front end of the catheter body 2, as illustrated in FIG. 2, a plurality of (three in this example) side holes 22 is provided in the axial direction to communicate with the blood removing lumen 10 and may withdraw blood between both the balloons 3 and 4 to the blood removing lumen 10. For example, a gap between the balloon 3 and the balloon 4 in which the side holes 22 are provided is set to 40 mm to 60 mm. The balloon 3 is a so-called flat balloon which can flatly adhere to an outer peripheral surface of the central portion 18 of the balloon base 5 in a deflated state without forming unevenness. For this reason, a wrinkle as in a conventional case is not formed.

According to the configuration of the base 5, as is clear from FIGS. 1 and 2, an outer peripheral surface of the base 15, to which the balloon 3 is attached, in the axial direction is inclined at the same angle as an inclination angle of the lumen 16, and thus the balloon 3 attached to the front end of the catheter body 2 through the balloon base 5 obliquely inflates since a line orthogonal to the central axis thereof is inclined at a predetermined angle θ with respect to the central axis of the catheter body 2 in an inflated state. The other balloon 4 attached to the catheter body 2 does not obliquely inflate since a line orthogonal to the central axis thereof is not inclined while being orthogonal to the central axis of the catheter body 2 in an inflated state.

In FIG. 1, reference numerals 23 and 24 denote connectors branched and provided at a rear end of a catheter body 2. The connector 23 communicates with the blood removing lumen 10, and the connector 24 communicates with the blood feeding lumen 11. A circulation tube having a blood purifier F and a pump P included in the mass administration system of the anticancer drug as a closed circuit described above is connected to the connector 23 and the connector 24, blood sent from the blood removing lumen 10 via the connector 23 is purified by the blood purifier F, and the purified blood is further circulated and sent to the blood feeding lumen 11 via the connector 24. In addition, reference numerals 25 and 26 similarly denote connecting connectors provided at the rear end of the catheter body 2, a syringe (not illustrated) is connected to these connecting connectors 25 and 26, and physiological saline is sent from the syringe to the balloons 3 and 4 via the balloon lumens 12 and 13.

Figure 6:
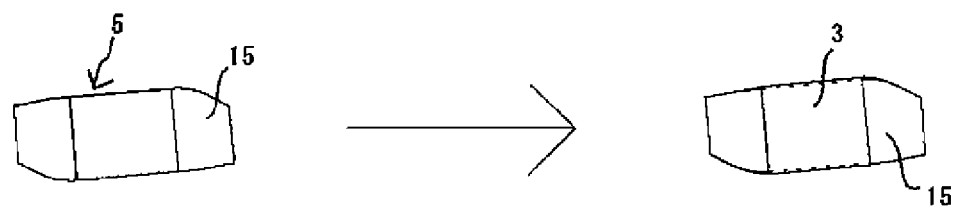
FIG. 6 is a diagram illustrating a state where a balloon is attached to the balloon base and a step between the balloon and the base is made gentle in a manufacturing process of the balloon catheter of the same.
Figure 7:
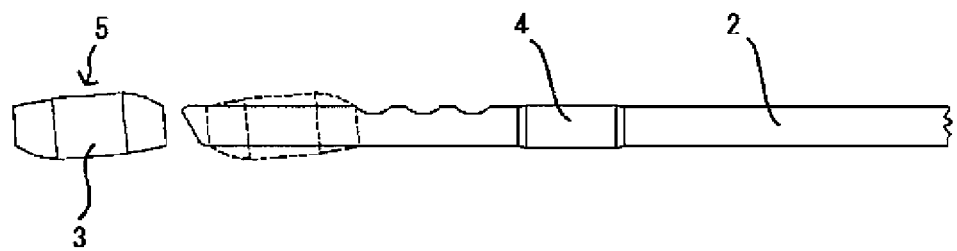
FIG. 7 is a diagram illustrating a state where the balloon base to which the balloon is attached is mounted and attached to a catheter body in the manufacturing process of the balloon catheter of the same.
Figure 8:
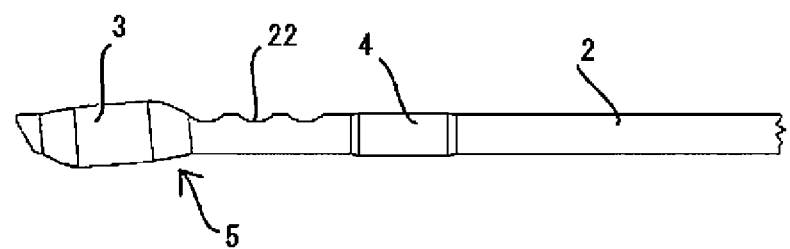
FIG. 8 is a diagram illustrating a completed state (balloon deflation) of the balloon catheter of the same.
Figure 9:
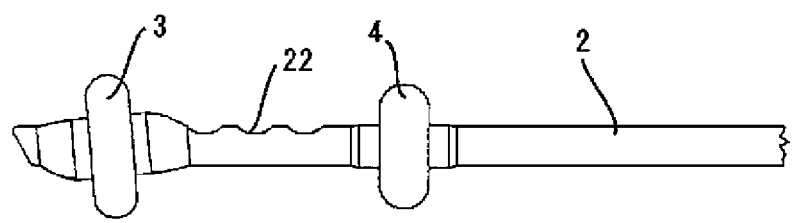
FIG. 9 is a diagram illustrating a completed state (balloon inflation) of the balloon catheter of the same.

FIGS. 6 to 9 are diagrams for description of a method of manufacturing the catheter. This method will be sequentially described as follows. That is, first, the balloon 3 is attached to the individually manufactured balloon base 5 (FIG. 6). This attaching operation is performed on the outer peripheral surface of the central portion 18 which is a flat cylindrical surface of the balloon base 5, and thus is not difficult and may be smoothly carried out. Thereafter, the balloon base 5 to which the balloon 3 is attached is inserted from the front end of the catheter body 2 (FIG. 7), and the balloon base 5 is attached and fixed to the catheter body 2 when a predetermined attachment position is reached (FIG. 8). A dotted line of FIG. 7 indicates an attachment assumed position of the base 5. When the balloon base 5 is inserted into the catheter body 2, since the lumen 16 of the balloon base 5 is substantially the same as the outer diameter of the catheter body 2, an inserted distal end of the catheter body 2 is bent and fit into the lumen 16 of the balloon base 5 by being adapted thereto. For this reason, the balloon base 5 is provided to be inclined by eccentricity of the balloon base 5 with respect to the catheter body 2 in a completed state (FIG. 8). That is, when the balloon 3 is inflated, the balloon 3 apparently inflates obliquely (FIG. 9). The inclination of the balloon 3 can be adjusted by changing an eccentric angle of the balloon base 5.

Figure 10:
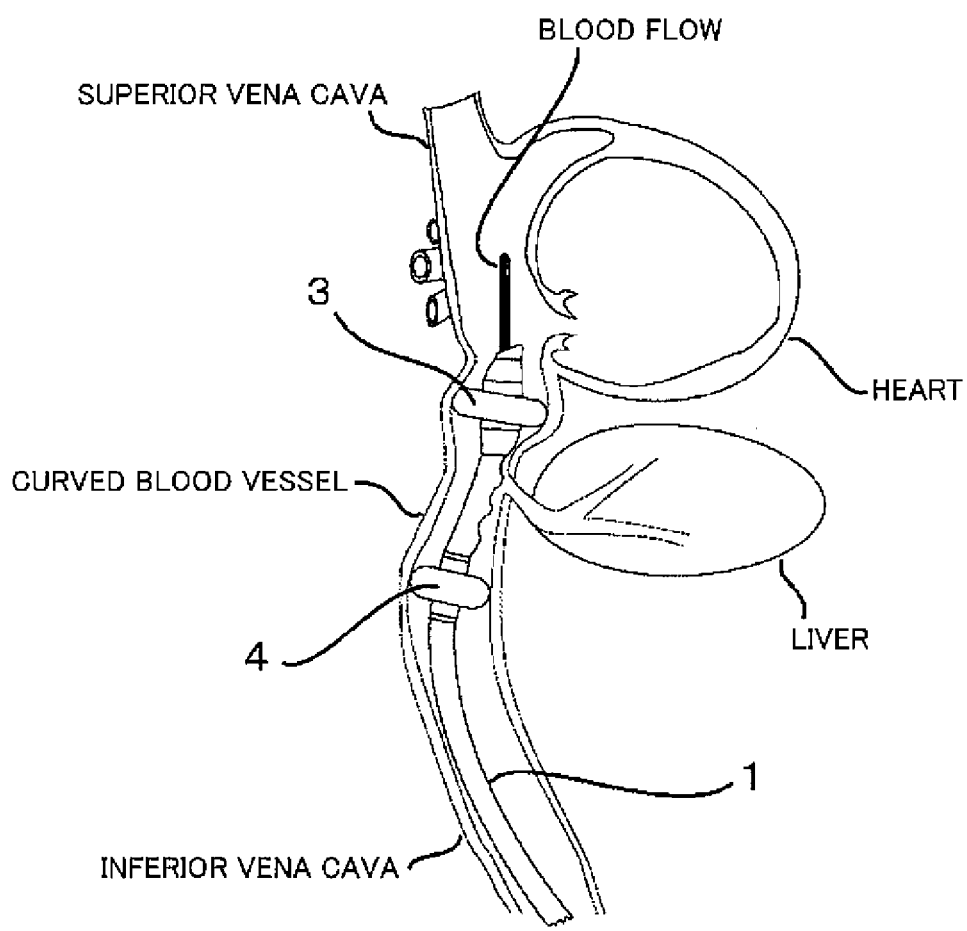
FIG. 10 is an operation explanatory view illustrating a state where the balloon catheter is inserted into a curved blood vessel of the same.
Figure 12:
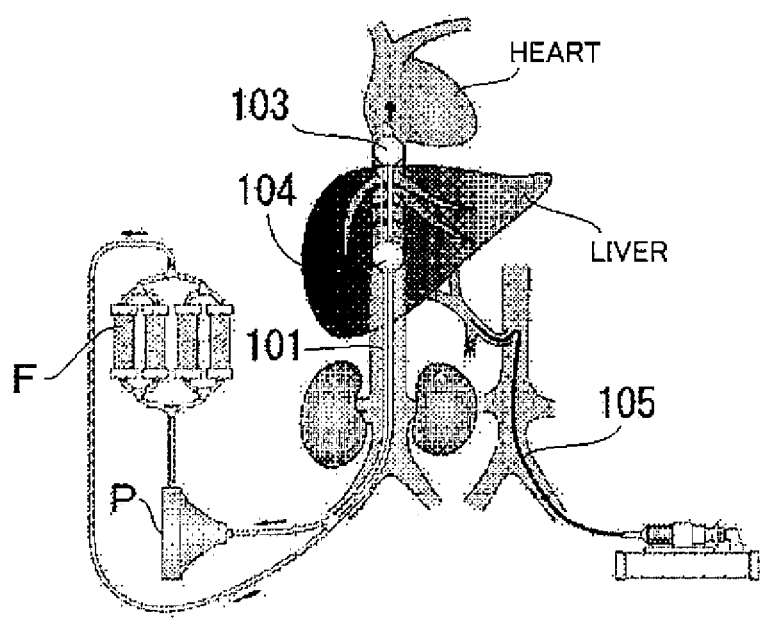
FIG. 12 is a schematic explanatory view illustrating an example of a conventionally known mass administration system of anticancer drug.
Figure 13:
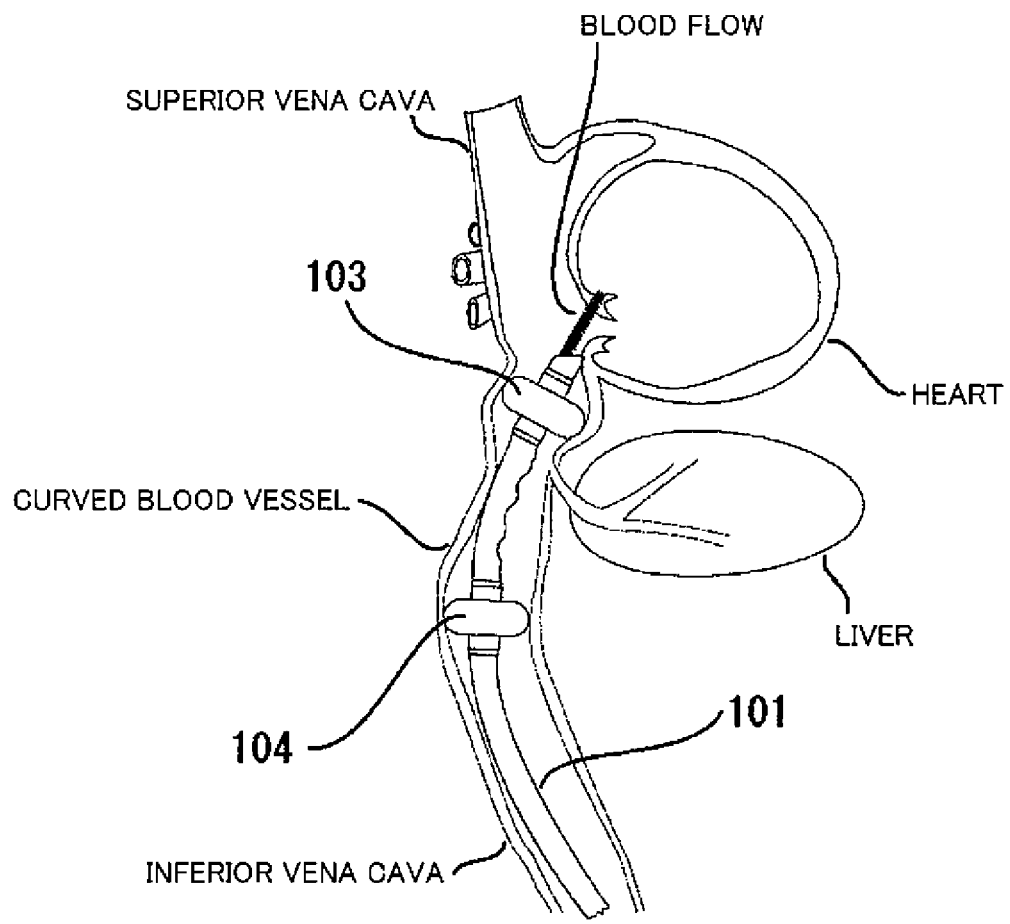
FIG. 13 is an operation explanatory view illustrating a state where a conventional balloon catheter is inserted into a curved blood vessel.

A method of using the balloon catheter 1 will be described. Basically, the method is similar to the content described in the conventional system for administering a large amount of anticancer drug to the patient with liver cancer illustrated in FIG. 12. The balloon catheter 1 is put in a blood vessel of the patient from a front end side thereof, and inserted into a curved blood vessel connecting the superior vena cava and the inferior vena cava close to the heart, so that the balloon 3 is located in the curved blood vessel. Then, when physiological saline is sent via the balloon lumens 12 and 13 and the balloons 3 and 4 are inflated, the balloons 3 and 4 hit the inner wall of the blood vessel and the balloon catheter 1 is indwelled and fixed (FIG. 10). In this instance, the balloon 3 is in an attachment state described above, and thus obliquely inflates to incline with respect to the catheter body 2. Meanwhile, when the connector 23 of the balloon catheter 1 is connected to one end of the circulation tube, and the connector 24 is connected to the other end of the circulation tube outside the body, the mass administration system of the anticancer drug against liver cancer is constructed in a closed circuit, and the system has a blood purification action in a state where the anticancer drug is continuously administered into the hepatic artery from the catheter 105 of the anticancer drug administration device as illustrated in FIG. 12. Upon blood purification action, a large amount of anticancer drug administered from the catheter 105 of the anticancer drug administration device is taken into the blood removing lumen 10 together with the hepatic venous blood from the side hole 22 provided in a occluded part between the two balloons 3 and 4. Thereafter, the blood is removed from the blood removing lumen 10, purified through the blood purifier F, and returned to the blood feeding lumen 11. The purified and returned blood is sent to the heart from the distal end opening of the balloon catheter 1 by bypassing the part occluded by the balloons 3 and 4.

In the operation of the system, the balloon 3 of the balloon catheter 1 obliquely inflates to incline with respect to the catheter body 2, and thus a central axis of a blood vessel does not shift from the central axis of the catheter body 2 even when the blood vessel is curved as illustrated in FIG. 10. For this reason, the blood flow is along the central axis of the blood vessel, and does not directly hit the blood vessel wall as illustrated in the drawing. In other words, unlike the conventional one, the central axis of the lumen of the curved blood vessel does not shift from the central axis of the catheter, and the blood flow does not directly hit the blood vessel wall to damage the blood vessel wall due to the rigidity of the catheter. In addition, even in the curved blood vessel, indwelling and fixing may be surely performed, and a contact area of the balloon 3 with respect to the blood vessel does not decrease. Thus, even in the deflated state of the balloon 3, adhesion to the outer peripheral surface of the balloon base 5 is allowed, and the balloon 3 does not slip due to pressure during blood feeding.

In addition, in the shaped balloon 175 cited as the conventional art, a wrinkle is generated in the balloon in a deflated state, and unevenness of the balloon occurs on the surface of the catheter. Thus, when the catheter of the shaped balloon is inserted into the blood vessel, there is concern that the inner wall of the blood vessel may be damaged due to the wrinkle of the balloon. However, the balloon 3 of the balloon catheter 1 is a flat balloon that can adhere to the outer peripheral surface of the base 5 in the deflated state and does not cause unevenness. Thus, even when the catheter is inserted into the lumen, the inner wall of the blood vessel is not damaged.

In this embodiment, the catheter body 2, the balloon base 5, and the balloons 3 and 4 are made of a material suitable for a living body such as silicone rubber, and this material includes thermoplastic resins such as PP, PE, PU, and nylon. Further, a material used in medical devices may be used.

<Modification>

Figure 11:
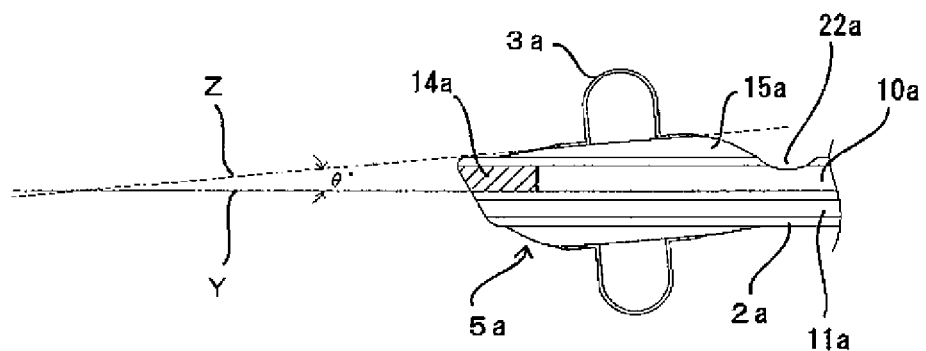
FIG. 11 is an enlarged cross-sectional view of a balloon portion corresponding to FIG. 2 illustrating a modification.

FIG. 11 illustrates a modification. The modification is basically different from the embodiment in that a balloon base 5a is formed integrally with a catheter body 2a and is the same as or similar to the embodiment in other respects. For this reason, a description of the same or similar configuration as that in the embodiment will be simplified by attaching an alphabet letter a to the same reference numeral as that in the embodiment.

In more detail, the balloon base 5a is integrally provided in a cylindrical shape having a larger diameter than an outer diameter of the catheter body at a front end of the catheter body 2a. In the balloon base 5a, as is clear from the drawing, an outer peripheral surface in an axis direction, in other words, a central axial formed by the outer peripheral surface is formed to incline at a predetermined angle θ° with respect to a central axis of the catheter body 2a, and a balloon 3a is provided on the outer peripheral surface. The balloon 3a is a flat balloon mentioned above, and obliquely inflates with respect to the central axis of the catheter body 2a in an inflated state. As described above, the predetermined angle θ° is preferably in a range of 3° to 10°. In the figure, Z denotes an axis extending along the outer peripheral surface of the balloon base 5a and intersecting the central axis Y of the catheter body 2a, and Z and Y form the predetermined angle θ°.

The embodiment is merely a preferable example, and design of details, etc. of the present invention may be appropriately modified and corrected within a range described in claims. For example, the inclination angle of the lumen 16 of the balloon base 5, the shape of the outer peripheral surface of the both ends 19 and 20 of the base 15, etc. may be appropriately designed in practice. In addition, the balloon base 5 may not be a separate body as shown in the example of the embodiment, and may be formed integrally with the catheter body 2a as shown in the modification. In addition, even though the embodiment shows an example in which the balloon catheter 1 is used for the mass administration system of the anticancer drug for the liver cancer patient, it goes without saying that the balloon catheter 1 may be used for another purpose.

The invention claimed is:

1. An oblique inflation type balloon catheter configured for use in a curved blood vessel connecting a superior vena cava and an inferior vena cava close to a heart, the balloon catheter comprising:
    a tubular catheter body having a predetermined length and a catheter lumen provided in an axis direction from a front end to a rear end thereof;
    a front end balloon provided on the front end of the tubular catheter body; and
    a cylindrical shaped balloon base having a larger diameter than an outer diameter of the catheter body integrally provided at the front end of the tubular catheter body and having a tubular shaped base,
    wherein a balloon base lumen having the same diameter as the outer diameter of the catheter body is formed within the tubular shaped base over an entire length with both ends opened, a central axis of the balloon base lumen is inclined at a predetermined lumen angle with respect to a central axis of the tubular shaped base concentric with a central axis of the catheter body, an outer peripheral surface in an axis direction is formed in parallel with the central axis of the tubular shaped base, and the outer peripheral surface of the parallel tubular shaped base includes an outer peripheral surface of a balloon attachment central portion parallel to the central axis of the tubular shaped base and an outer peripheral surface of both ends curved to have a diameter gradually decreasing from the central portion, the front end balloon is provided on the outer peripheral surface of the balloon attachment central portion to obliquely inflate with respect to the central axis of the catheter body during inflation.

2. The oblique inflation type balloon catheter according to claim 1, wherein the catheter lumen of the tubular catheter body is partitioned into a blood removing lumen for removing blood from a blood vessel and a blood feeding lumen for sending blood to the blood vessel, and an opening area of the blood removing lumen is larger than an opening area of the blood feeding lumen.

3. The oblique inflation type balloon catheter according to claim 2, wherein further a second balloon is provided in the catheter body at a predetermined length behind the front end balloon, and a side hole for taking blood into the blood removing lumen is provided in the tubular catheter body between the second balloon and the front end balloon.

4. The oblique inflation type balloon catheter according to claim 1, wherein the predetermined lumen angle is in a range of 3° to 10°.

* * * * *